United States Patent [19]
Ommaya

[11] Patent Number: 5,385,582
[45] Date of Patent: * Jan. 31, 1995

[54] SPINAL FLUID DRIVEN ARTIFICIAL ORGAN

[76] Inventor: Ayub K. Ommaya, 8006 Glennbrook Rd., Bethesda, Md. 20814

[*] Notice: The portion of the term of this patent subsequent to Jun. 29, 2010 has been disclaimed.

[21] Appl. No.: 103,244

[22] Filed: Aug. 9, 1993

Related U.S. Application Data

[63] Continuation-in-part of Ser. No. 653,635, Feb. 11, 1991, abandoned.

[51] Int. Cl.$^6$ ............................................. A61F 2/04
[52] U.S. Cl. ........................................ 623/12; 604/9; 604/890.1
[58] Field of Search ...................... 623/12; 604/4–6, 604/8–10, 890.1, 891.1, 892.1

[56] References Cited

U.S. PATENT DOCUMENTS

| | | |
|---|---|---|
| 4,201,845 | 5/1980 | Feder et al. |
| 4,479,796 | 10/1984 | Kallok |
| 4,559,299 | 12/1985 | Rotman |
| 4,878,913 | 11/1989 | Aebsicher et al. |
| 4,892,538 | 1/1990 | Aebischer et al. |
| 4,954,251 | 9/1990 | Barnes et al. |
| 5,011,472 | 4/1991 | Aebischer et al. |
| 5,026,650 | 6/1991 | Schwarz et al. |
| 5,222,982 | 6/1993 | Ommaya |

FOREIGN PATENT DOCUMENTS

| | | |
|---|---|---|
| 0155237 | 9/1985 | European Pat. Off. |
| 0398083 | 11/1990 | European Pat. Off. |
| 0421380 | 4/1991 | European Pat. Off. |
| 2569987 | 3/1986 | France |
| 2225862 | 12/1973 | Germany |
| 3710794 | 11/1988 | Germany |
| 3-224474 | 10/1991 | Japan |
| WO90/15637 | 12/1990 | WIPO |

OTHER PUBLICATIONS

Skolnick, A., "Advances in Islet Cell transplantation: Is Science Closer to a Diabetes Cure?", *JAMA* (1990), vol. 264, pp. 427–428.

Scharp, D. W., et al., "Insulin Independence After Islet Transplantation Into Type I Diabetic Patient", *Diabetes* (1990), vol. 39, pp. 515–518.

Bretzel, R. G., et al. "Islet Transplantation in Diabetes Mellitus", in *Diabetes and the Kidney* (1989), vol. 73, pp. 217–228.

Tze, W. J., et al., "Intrathecal Allotransplantation of Pancreatic Endocrine Cells in Diabetic Rats", *Transplantation* (1986), vol. 41, pp. 531–534.

Morris, P. J., et al., "Pancreatic Islet Transplantation", *Brit. Med. Bull.* (1989), vol. 45, pp. 224–241.

Barneo, L., et al., "Comparison of Various Techniques for Rat Islet Preparation", *Transplantation Proc.* (1990), vol. 22, pp. 777–778.

Winoto, S., et al., "Magnetic Microspheres (MMS) Coupled to Selective Lectins", *Transplantation Proc.* (1989), vol. 21, pp. 2628–2630.

(List continued on next page.)

*Primary Examiner*—David H. Willse
*Attorney, Agent, or Firm*—Beveridge, DeGrandi, Weilacher & Young

[57] ABSTRACT

The present invention concerns a spinal fluid driven artificial organ device and methods for its use. The device 10 has a tripartite chamber with three sections. A micropore filter B separates chamber section 1 from chamber section 2 and a micropore filter C separates chamber section 2 from chamber section 3. CSF enters chamber section 1 via an inlet tube T1 and an one way value V1. Micropore filter B allows entry of CSF into chamber section 2 but does not allow exit of any cells from chamber section 2 into chamber section 1. Micropore filter C allows free passage of CSF from chamber section 2 into chamber section 3 and prevents any cells in chamber section 2 from entering chamber section 3. The CSF flow exits chamber section 3 via an one way valve V2 and all outlet tube T2. The outlet tube T2 delivers the CSF to the desired location.

21 Claims, 3 Drawing Sheets

OTHER PUBLICATIONS

Van der Burg, M. P. M., et al., "Comparison of Islet Isolation Techniques in Dogs", *Transplantation Proc.* (1990), vol. 22, pp. 795–796.

Joslin, J. A., et al., "Isolation and Extended Culture of Porcine Fetal Islets", *Transplantation Proc.* (1990), vol. 22, p. 794.

Hesse, U. J., et al., "Preparation and Transplantation of Pancreatic Islet Tissue in Landrace Pigs and the Munich Miniature Swine Troll", *Transplantation Proc.* (1990), vol. 22, p. 793.

London, N. J. M., et al., "A Simple but Effective Method for the Controlled Collagenase Digestion of the Human Pancreas", *Transplantation Proc.* (1990), vol. 22, pp. 791–792.

Calafiore, R., et al., "A Simple Method for Bulk Separation of Highly Purified Human Islets of Langorhans", *Transplantation Proc.* (1990), vol. 22, pp. 789–790.

Ricordi, C., et al., "Application of the Automated Method to Islet Isolation in Swine", *Transplantation Proc.* (1990), vol. 22, pp. 784–785.

Soon-Shiong, P., et al., "Islet Preparation by a Novel Immunomicrosphere Cell Depletion Technique", *Transplantation Proc.* (1990), vol. 22, pp. 780–781.

Ohzato, H., et al., "Intraductal Injection of Collagenase Solution at the Time of Harvesting", *Transplantation Proc.* (1990), vol. 22, pp. 782–783.

Sutton, R., et al., "Human Pancreatic Islet Isolation with Increased Incubation Temperatures and Variable Density Gradients", *Transplantation Proc.* (1990), vol. 22, pp. 758–759.

Kover, K., et al., "Development of a Method for the Isolation of True Islets from Human Fetal Pancrease", *Transplantation Proc.* (1990), vol. 22, pp. 761–762.

Kneteman, N. M., et al., "Islet Isolation from Huan Pacrease Stored in UW Solution for 6 to 26 Hours", *Transplantation Proc.* (1990), vol. 22, pp. 763–764.

Kaufman, D. B., et al., "Canine Islet Autografts", *Transplantation Proc.* (1990), vol. 22, pp. 771–774.

Farkas, G., et al., "Alteration in Diabetic Retinopathy and Nephropathy Following Islet Transplantation", *Transplantation Proc.* (1990), vol. 22, pp. 765–766.

Woehrle, M., et al., "The Effect of Early Islet Transplantation on Prevention of Nephropathy in the Spontaneously Diabetic BB Rat", *Transplantation Proc.* (1990), vol. 22, pp. 819–820.

Galletti, P. M., "The Concept of Bioartificial Endocrine Organs", *Colloque INSERM* (1989), vol. 177, pp. 3–12.

Fan, M., et al., "Reversal of Diabetes in BB Rats by Transplantation of Encapsulated Pancreatic Islets", *Diabetes* (1990), vol. 39, pp. 519–522.

Wu, Z. G., et al., "In Vitro Culture and Transplantation of Encapsulated Human Fetal Islets as an Aritifical Endocrine Pancrease", *Trans. Am. Soc. Artif. Intern. Organs* (1989), vol. 35, pp. 736–738.

Sun, A. M., "Microencapsulation of Pancreatic Islet Cells", *Methods in Enzymology* (1988), vol. 137, pp. 575–580.

Moumar, A. A. B., et al., "Realization of a Bioartificial Pancrease Using a New Performant Asymetric Membrane", *Colloque INSERM* (1989), vol. 177, pp. 209–214.

Notelet, D., et al., "Pancreas Bioartificial", *Colloque INSERM* (1989), vol. 177, pp. 231–236.

Siebers, U., et al., "Histocompatibility of Semi-permeable Membranes for Implantable Diffusion Devices (Bioartificial Pancreas)", *Transplantation Proc.* (1990), vol. 22, pp. 834–835.

Jansson, L., et al., "The Blood Perfusion of Auto-transplanted Pancreatic Islets in the Rat", *Transplantation Proc.* (1990), vol. 22, pp. 775–776.

Menger, M. D., et al., "The Microvasculature of Xenogeneic Transplanted Islets of Langerhans", *Transplantation Proc.* (1990), vol. 22, pp. 802–803.

Warnock, G. L., et al., "Effect of Diabetes on the Function of Transplanted Human Islets of Langerhans", *Transplantation Proc.* (1990), vol. 22, pp. 804–805.

Manin, M., et al., "Metabolic Clearance of Insulin From the Cerebrospinal Fluid in the Anesthetized Rat", *Peptides* (1990), vol. 11, pp. 5–12.

Wallum, B. J., et al., "Cerebrospinal Fluid Insulin Levels Increase During Intravenous Insulin Infusions in Man", *J. Clin. Endocrinology and Med.* (1987), vol. 64, pp. 190–194.

Strubbe, J. H., et al., "Insulin Responses and Glucose Levels in Plasma and Cerebrospinal Fluid During Fasting and Refeeding in the Rat", *Physiology and Behavior* (1988), vol. 44, pp. 205–208.

Steffens, A. B., et al., "Penetration of Peripheral Glucose and Insulin into Cerebrospinal Fluid in Rats", pp. R200–R204.

Tze, W. J., et al., "Immunological Studies in Diabetic Rat Recipients with a Pancreatic Islet Cell Allograft in the Brain", *Transplantation* (1989), vol. 47, pp. 1053–1057.

SPINAL FLUID DRIVEN ARTIFICIAL ORGAN

This application is a continuation of PCT/US92/00947 which designates the U.S. and has an international filing date of 7 Feb. 1992, which, in turn, is a continuation-in-part of U.S. Ser. No. 07/653,635 filed 11 Feb. 1991, now abandoned.

BACKGROUND OF THE INVENTION

The present invention concerns a spinal fluid driven artificial organ device and a method for its use. In particular, this artificial organ, when it contains pancreatic islet cells, can be utilized to treat Type I diabetes mellitus. In addition, the artificial organ can be utilized with other types of cells in order to treat a whole range of diseases requiring endocrine replacement therapy.

Transplantation of islets of langerhans, including intracerebral or intrathecal transplantation, has been proposed to treat diabetes (Jansson, L., and S. Sandlet, *Transplantation Proceedings* (1990), volume 22, pages 775-776; Tze et al, *Transplantation* (1986), volume 41, pages 531-534). However, the number of islets needed to cure diabetes in rodents is so large that the size of the graft usually exceeds the diffusion distance for oxygen (Jansson, L., and S. Sandler, *Transplantation Proceedings* (1990), volume 22, pages 775-776), and revascularization can lead to graft rejection (Menger, M. D., S. Jaeger, P. Walter, F. Hammersen, and K. Messmer, *Transplantation Proceedings* (1990), volume 22, pages 802-803). The diabetic state itself can also adversely affect islet transplantation (Warnock, G. L., N. M. Kneteman, and R. V. Rajotte, *Transplantation Proceedings* (1990), volume 22, pages 804-805). In addition, there is growing evidence that type I (insulin dependent) diabetes is an autoimmune disease. The immunogenicity of islet cells remains a major obstacle to the use of islet transplantation (Sun, A. M., *Methods in Enzymology* (1988), volume 137, page 576). Thus, graft rejection and autoimmune destruction of transplanted pancreatic islets are major problems (Fan, M., Z. Lum, X. Fu, L. Levesque, I. Tai and A. Sun, *Diabetes* (1990), volume 39, page 519).

Current attempts to ameliorate the effects of Parkinsonism by using adrenal cells or fetal substantia nigra cells transplanted directly into the brains of humans have produced transient improvements only. Moreover, the long term effects and possible auto-immune reactions to such direct intracerebral transplants is a continuing cause for concern.

The possibility of utilizing live tissue in all implantable device, comprised of a synthetic membrane, for the purpose of organ replacement was first established in the late 1970s (Galletti, P. M., *Colloque Inserm* (1989), volume 177, pages 3-12). Such immuno-isolated transplants must have a permeable membrane which allows the transport of nutrients and chemical messengers from the environment to the tissue and which allows the release of effector substances from that tissue into the appropriate body site. Some requirements of the membrane are described in Galletti, P. M., "The Concept of Bioartificial Endocrine Organs", *Colloque Inserm* (1989), volume 177, pages 3-12.

In general, two techniques have been utilized: microencapsulation and macroencapsulation. Microencapsulation involves encapsulating a cell or cell cluster with a permeable polymer gel with subsequent injection into the body. Macroencapsulation involves sealing cell suspensions into permeable tubular membranes and subsequently implanting the tubes into the body. Use of immuno-isolated transplants has been proposed to treat type I (insulin dependent) diabetes. Microencapsulation of islet cells has been used to treat diabetes in rats and humans (Fan, M., Z. Lum, X. Fu, L. Levesque, I. Tai and A. Sun, *Diabetes* (1990), volume 39, page 519; Wu, Z. G., Z. Q. Shi, Z. N. Lu, H. Yang, F. Y. Shi, X. R. Zheng, and A. M. Sun, *Trans. Am. Soc. Artif. Intern. Organs* (1989), volume 35, pages 736-738). However, disadvantages of microencapsulation and macroencapsulation include (1) biocompatibility of the artificial membrane, (2) fibrosis associated with tubes which inhibit the entrance of nutrients and oxygen and the exit of products, thus compromising in vivo survival of the cells and preventing the device from being operable for a sufficient time, and (3) long diffusion distances associated with thick membranes or large tissue chambers.

The present invention lacks the disadvantages and shortcomings of the prior art and provides a spinal fluid driven device and method for treating diseases. One advantage of the present device is that it will successfully isolate cells from the problem of the abnormal microangiopathic environment and it makes it much easier to control the hyperglycemic state because of the lag between the blood sugar level and the spinal fluid level, which tends to be slower to respond to changes in blood sugar level, thus blunting the effects of sudden surges in blood sugar level.

SUMMARY OF THE INVENTION

One of the objects of the present invention is to provide a spinal fluid driven artificial organ that can be utilized in treating disease such as diabetes. The device is constructed primarily of medical grade silicon rubber identical to that used in chronically implantable devices placed in subcutaneous regions of the body such as the Ommaya Reservoir and the Pudenz Hydrocephalus shunting device. Either allografts or xenografts will be introduced into a central chamber through which a one-way flow of cerebrospinal fluid will pass via two micropore filters. This arrangement enables the cerebrospinal fluid to function in three roles: (a) as a nutrient for the grafts, (b) as a source of chemical signals to the graft, and (c) as a fluid flow enabling transfer of the graft secretions to the host's body.

BRIEF DESCRIPTION OF THE DRAWINGS

FIG. 3A shows spinal-peritoneal system placement. FIG. 3B and 3C show ventriculo-cisternal system placement. FIG. 3D shows spinal-vascular system placement.

DETAILED DESCRIPTION OF THE INVENTION

The spinal fluid driven artificial organ 10 is an implantable neurosurgical device which enables the transfer of cerebrospinal fluid (CSF) from the spinal CSF space to the artificial organ and then into the peritoneal space or other absorptive space, such as blood vessels, or back into cerebrospinal fluid.

Figure 1:
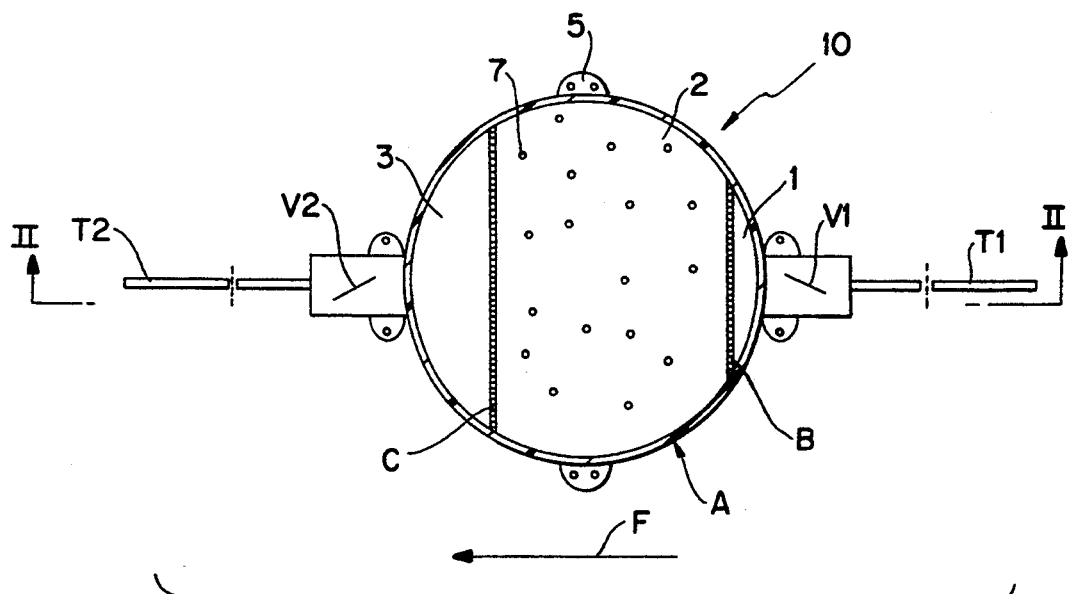
FIG. 1 shows a top, cross-sectional view of the spinal fluid driven artificial organ with the cross-section taken at level I—I in FIG. 1.
Figure 2:
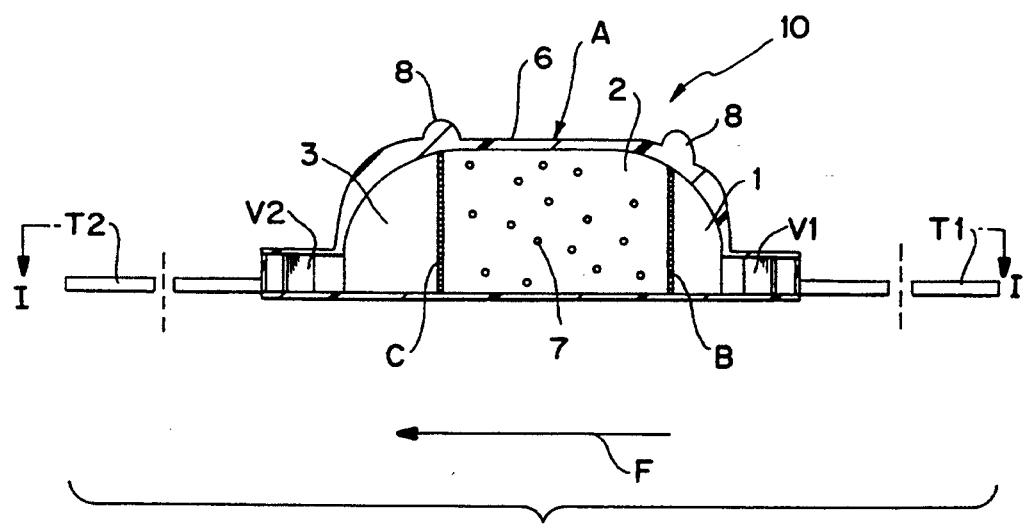
FIG. 2 shows a side, cross-sectional view of the spinal fluid driven artificial organ with the cross-section taken at level II—II in FIG. 1.

With reference to FIGS. 1 and 2, there is shown the spinal fluid driven artificial organ 10. The tripartite chamber "A" has three sections (1, 2, 3). Micropore filter "B" separates chamber section 1 from chamber section 2. Micropore filter "C" separates chamber section 2 from chamber section 3. CSF enters chamber section 1 via an inlet tube (T1) and a one way valve (V1). Micropore filter "B" allows entry of CSF into chamber section 2 but does not allow exit of any cells from chamber section 2 into chamber section 1. Micropore filter "C" allows free passage of CSF from chamber section 2 into chamber section 3 and prevents any cells in chamber section 2 from entering chamber section 3. The CSF flow exits chamber section 3 via a one way valve (V2) and all outlet tube (T2). The outlet tube (T2) delivers the CSF to the desired location.

Figure 3A:
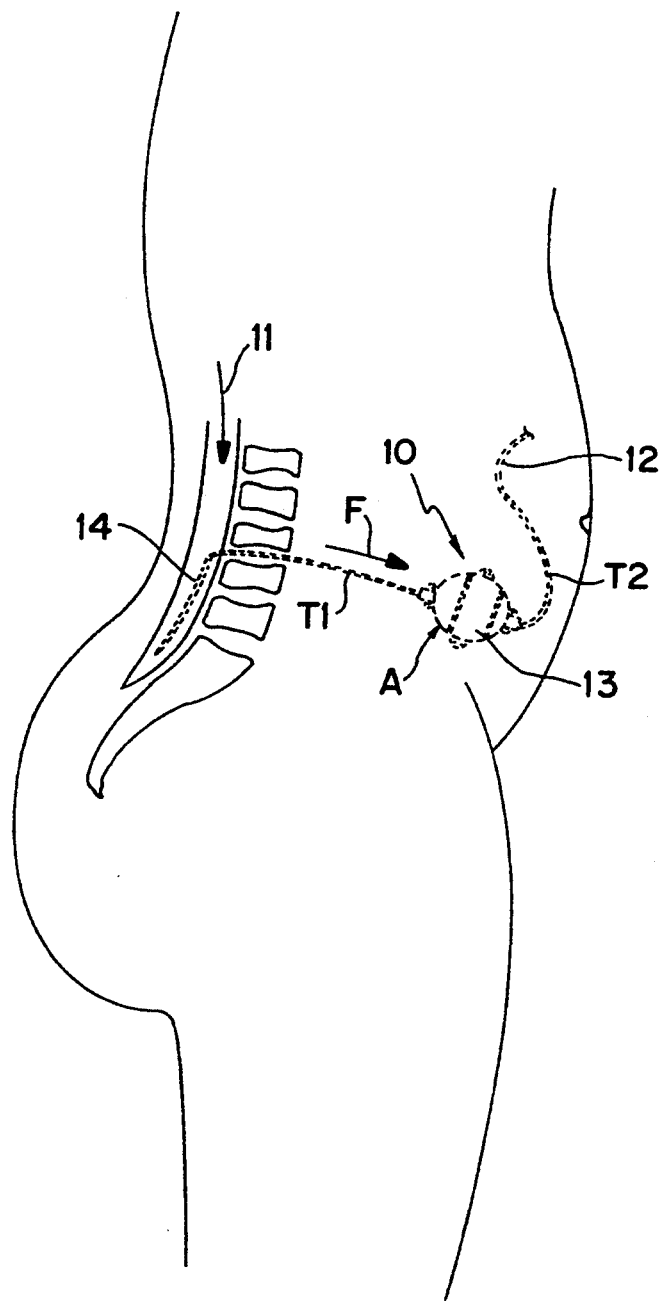
FIGS. 3A-3D shows three possible placements of the spinal fluid driven artificial organ in a patient depending on how the cerebrospinal fluid is caused to flow through the system. The device itself is always placed in a sub-cutaneous location.
Figure 3B:
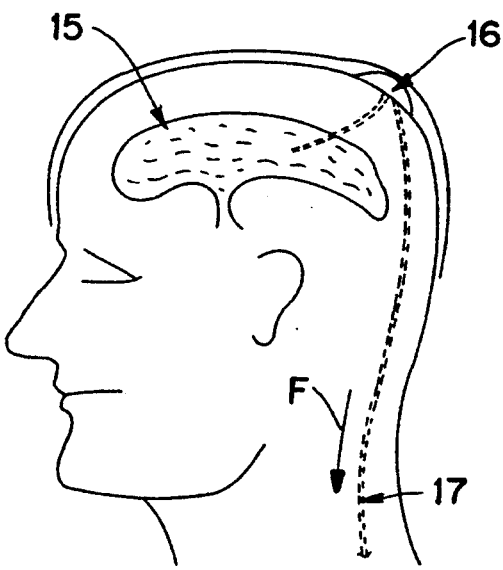
Figure 3C:
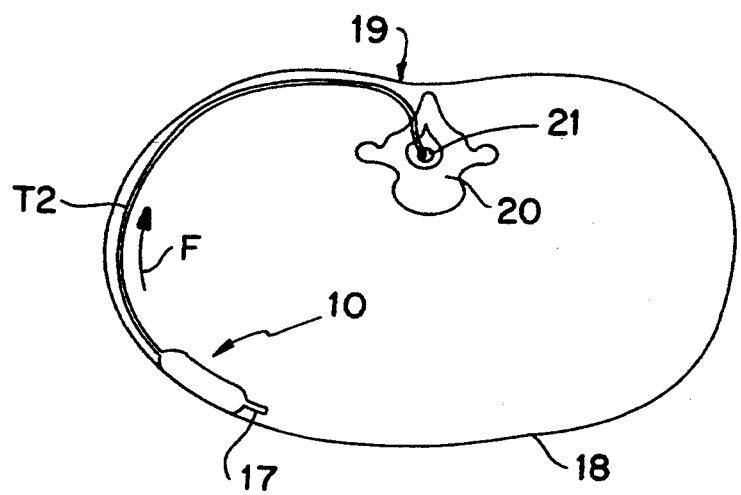
Figure 3D:
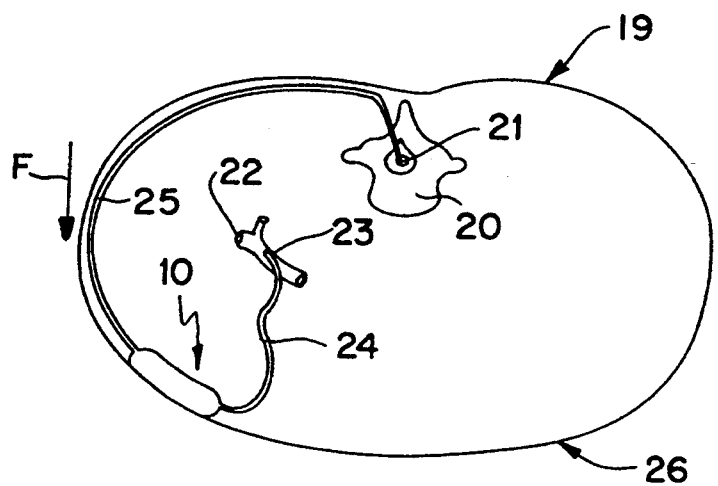

Depending on the disease indication which is to be treated, the placement of the device and its input/output catheters (tubes) can be any one of three locations: ventriculo-spinal for diseases requiring hormonal substances to be delivered primarily to the central nervous system, spinal-peritoneal or spinal-vascular for diseases requiring hormonal substances to be delivered to other body systems. FIG. 3A depicts tire spinal-peritoneal placement indicated for the delivery of insulin from islet cells in the device chamber in cases of insulin dependent diabetics. FIGS. 3B and 3C depict the ventriculo-cisternal placement for delivery of dopamine from substantia nigra grafts to the central nervous system. FIG. 3D depicts the spinal-vascular placement for indications similar to that needing the spinal-peritoneal (3A) placement. In any and all of these three types of placement, the artificial organ chamber part will always be in a subcutaneous location, only tire input and output tubes being differently placed as shown in FIG. 3A.

Central chamber section 2 contains the desired transplanted cells 7. The desired cells are loaded into chamber section 2 by subcutaneous injection through the self-sealing, repeatedly punctureable dome 6 of chamber "A". The CSF flowing from chamber section 1 into chamber section 2 nourishes the cells and provides a signal to the cells to produce products (e.g., to make insulin). The CSF flowing through chamber section 2 provides the motive power to carry secreted products from the cells through micropore filter "C" into chamber section 3.

Because the CSF flow is only in the one direction (designated F) and because of the motor force provided by the CSF flow through, cellular material from other sites in time body cannot migrate against the CSF flow to enter organ chamber "A". Thus, there will be no threat to the immunological isolation of the cells in chamber section 2. The desired cells in chamber section 2 can be easily placed, replenished or removed for replacement by fresh transplants as needed by simple subcutaneous injection through the dome of chamber "A". The dome 6 is easily identified by location of two ridges 8, marking the locations of the two micropore filters "B" and "C" (see FIG. 2), under the overlying skin. The quality of the hormonal content of CSF reaching chamber section 3 can also be easily assayed, through the use of a syringe and suitable hypodermic needle, by subcutaneous sampling of the fluid in chamber section 3. Artificial organ 10 is secured to fascia (not shown) through use of flanges 5 preferably formed by dacron or silicon.

The desired cells in chamber section 2 may be insulin secreting pancreatic islet cells. The cells may be from any source (e.g., human cadavers, pigs, etc.). The cells may be from a cryopreserved source. Other types of cells which may be used will be, for example, fetal substantia nigra cells for treating patients with Parkinsonism or growth hormone secreting cells for treating patients with growth deficiencies.

All of the above cells may be isolated and treated according to known methods, e.g., Scharp, D. W., et al., *Diabetes* (1990), volume 39, pages 515-6; Z. Lum, X. Fu, L. Lavesqua, I. Tai and A. Sun, *Diabetes* (1990), volume 39, page 519); Sun, A. M., *Methods in Enzymology* (1988), volume 137, page 576; and Warhock, G. L., D. K. Ellis, and R. V. Rajotte, *Transplantation* (1988), page 957.

Chamber "A" is generally made of medical grade silicon rubber reinforced at suitable sites with dacron or teflon mesh. All materials to be used are available and have been used for chronic implanted devices for many years in patients.

The inlet tube (T1) and outlet tube (T2) are approximately 1 mm in diameter. These tubes are generally made of medical grade silicon rubber.

Micropore filters "B" and "C" have pores or about $1-5\mu$ in diameter and are commercially available. The filters are impermeable to cells and effector molecules of the immune system, thus providing total protection to transplanted islets against rejection. The filter does allow transport of small molecular nutrients, hormones and metabolites.

The desired location for delivery of the CSF by thee outlet tube (T2) may be the peritoneal space when insulin secreting pancreatic islet cells are placed in chamber section 2, thus enabling physiological control of diabetes mellitus (Type I). Other systemic hormonal deficiency diseases may be similarly treated when the appropriate cells are utilized in chamber section 2 (e.g., substantia nigra cells which secrete dopamine). The output from the outlet tube (T2) may be directed back into the CSF space if a central nervous system deficiency state (e.g., Parkinson's Disease) is to be corrected by the appropriate delivery of a neurotransmitting hormone or trophic factor produced by the appropriate cells implanted in chamber section 2.

FIG. 3A shows a spino-peritoneal placement of Artificial Organ 10 in, for example, a patient with Diabetes Mellitus Type I. In FIG. 3A the reference numbers listed below depict the following:

11—CSF containing spinal thecal sac
12—extension of outlet tube T2 in peritoneal cavity
13—chamber A positioned below skin in lower abdominal quadrant
14—spinal intrathecal inlet tube T1 enabling CSF flow to Artificial Organ chamber.

FIG. 3B and 3C show Artificial Organ 10 in a ventriculo-cisternal system placement. In FIG. 3B reference numbers depict the following:

15—cerebral ventricular cavity with CSF
16—flushing valve (one way)
17—subcutaneous outflow CSF catheter FIG. 3C shows a cross-section of the body at a L$\frac{3}{4}$ level. As shown in FIG. 3C, catheter 17 provides an inlet tube for the CSF flowing into artificial organ 10. The below listed reference numbers depict the following in FIG. 3C:

18—front of lower abdomen (cross-section)
19—back of person
20—spine of person
21—spina CSF space FIG. 3D shows a cross-section of the abdomen and a spinal-vascular system placement of the artificial organ 10. The below listed reference numbers depict the following in FIG. 3D:

22—large intra abdominal vein (e.g., portal vein)
23—intravascular catheter with slit valve at tip
24—intra abdominal outflow catheter entering vein
25—subcutaneous CSF inflow catheter.

Further variations and modifications of the invention will become apparent to those skilled in the art from the foregoing and are intended to be encompassed by the claims appended hereto.

What is claimed:

1. A method for treating diseases in a human or mammal, comprising:
   implanting an artificial organ in a body portion of the human or mammal, said artificial organ having an inlet port, an outlet port, an internal chamber, an inlet micropore filter and an outlet micropore filter, said implanting of said artificial organ including positioning said artificial organ such that said artificial organ receives cerebrospinal fluid from the human or mammal so that the fluid passes through said inlet port, passes unimpeded through said inlet micropore filter, passes through said internal chamber, passes unimpeded through said outlet micropore filter and passes out said outlet port; and
   introducing product-secreting cells into said internal chamber such that the product-secreting cells come in contact with the cerebrospinal fluid passing through the internal chamber and such that the product-secreting cells are prevented from exiting said internal chamber with the cerebrospinal fluid due to said outlet micropore filter.

2. A method as recited in claim 1 wherein introducing product-secreting cells includes injecting the cells between said inlet and outlet micropore filters.

3. A method as recited in claim 1 wherein cerebrospinal fluid flow through said artificial organ is in one direction.

4. A method as recited in claim 1 wherein the exiting cerebrospinal fluid with secreted product is introduced into a peritoneal space or other absorptive space following exiting said outlet port.

5. A method as recited in claim 1 wherein the exiting cerebrospinal fluid with secreted product is introduced back into cerebrospinal fluid.

6. A method as recited in claim 1 wherein implanting the artificial organ includes spinal-peritoneal system placement.

7. A method as recited in claim 1 wherein implanting the artificial organ includes vertriculo-cisternal system placement.

8. A method as recited in claim 1 wherein implanting the artificial organ includes spinal-vascular system placement.

9. A method as recited in claim 1 wherein introducing cerebrospinal fluid to said inlet port includes passing the cerebrospinal fluid through an inlet tube and past a one way valve positioned upstream from the chamber.

10. A method as recited in claim 9 wherein the cerebrospinal fluid exits said artificial organ through an exit tube having a one way valve.

11. A method as recited in claim 1 wherein the cerebrospinal fluid exits said artificial organ through an exit tube having a one way valve.

12. A method as recited in claim 1 wherein introducing the cells includes introducing allografts or xenografts by a subcutaneous injection through a self-sealing, repeatedly puncturable material forming said artificial organ.

13. A method as recited in claim 1 wherein the inlet and outlet micropore filters have pores of about 1–5μ.

14. A method as recited in claim 1 wherein introducing cells includes introducing insulin secreting pancreatic islet cells to the chamber to treat diabetes mellitus.

15. A method as recited in claim 1 wherein introducing cells includes introducing substantia nigra cells to treat Parkinsonism.

16. A method as recited in claim 1 wherein the flow of cerebrospinal fluid through said artificial organ is solely physiologically generated.

17. A method for treating diseases in a human or mammal, comprising:
   implanting an artificial organ in a body portion of the human or mammal, said artificial organ having an inlet tube, an outlet tube, an internal chamber in communication with said inlet and outlet tube, an inlet micropore filter positioned, with respect to a fluid flow through said artificial organ, between said inlet and outlet tubes, add an outlet micropore filter positioned, with respect to the fluid flow, between said inlet micropore filter and said outlet tube,
   positioning said inlet tube in contact with a source of cerebrospinal fluid such that the cerebrospinal fluid flows through said artificial organ and wherein said method for treating diseases is a passive method in that fluid flow into, through and out of said artificial organ is solely physiologically generated; and
   introducing product-secreting cells between said inlet and outlet micropore filters such that the product-secreting cells come in contact with the cerebrospinal fluid passing through said artificial organ.

18. A method as recited in claim 17 wherein introducing cells includes introducing insulin secreting pancreatic islet cells to the chamber to treat diabetes mellitus.

19. A method as recited in claim 17 wherein introducing cells includes introducing substantia nigra cells to treat Parkinsonism.

20. A method as recited in claim 17 wherein the flow of cerebrospinal fluid is unimpeded by said micropore filters.

21. A method for treating diseases in a human or mammal, comprising:
   implanting an artificial organ in a body portion of the human or mammal, said artificial organ having a chamber housing with an inlet, an outlet, and an internal chamber formed therein, said artificial organ further comprising an inlet micropore filter section and an outlet micropore filter section, and said implanting of said artificial organ including positioning said artificial organ such that said artificial organ receives cerebrospinal fluid from the human or mammal so that the fluid passes through said inlet, through said inlet micropore filter section, through said internal chamber, through said outlet micropore filter section and out said outlet, and said artificial organ further comprising an inlet tube having a free end in fluid communication with a source of said fluid and a second end in fluid communication with the inlet of said housing as well as an outlet tube extending away and in fluid communication with the outlet of said housing, introducing product-secreting cells into said internal chamber such that the product-secreting cells come in contact with the cerebrospinal fluid passing through the internal chamber and such that the product-secreting cells are prevented from exiting said internal chamber with the cerebrospinal fluid due to said outlet micropore filter section, and wherein said method for treating diseases is a passive method in that the passage of fluid through said inlet tube, housing, and outlet tube is based solely on physiologically generated forces of said human or mammal.

* * * * *